United States Patent [19]
Gitler et al.

[11] Patent Number: 5,204,239
[45] Date of Patent: Apr. 20, 1993

[54] BIOSENSORS INCLUDING LIPID BILAYER DOPED WITH ION CHANNELS ANCHORED TO A RECORDING ELECTRODE BY BRIDGING MOLECULES

[75] Inventors: Carlos Gitler; Itzhak Yuli, both of Rehovot, Israel

[73] Assignee: Yeda Research and Development Co., Ltd., Rehovot, Israel

[21] Appl. No.: 638,488

[22] Filed: Jan. 9, 1991

[30] Foreign Application Priority Data

Jan. 9, 1990 [IL] Israel ......................... 93020

[51] Int. Cl.[5] .................. C12Q 1/00; G01N 33/53; G01N 33/566; C12M 1/40
[52] U.S. Cl. .................... 435/7.1; 435/817; 435/288; 435/291; 436/525; 436/527; 436/501
[58] Field of Search ............... 435/877, 7.1, 817, 288, 435/291; 436/525, 527, 526, 501

[56] References Cited

U.S. PATENT DOCUMENTS

| | | | |
|---|---|---|---|
| 4,434,236 | 2/1984 | Freytag | 436/512 |
| 4,637,861 | 1/1987 | Krull et al. | 204/1 T |
| 4,895,809 | 1/1990 | Schlabach et al. | 436/518 |

FOREIGN PATENT DOCUMENTS 158834 10/1985 European Pat. Off. .
89011599 2/1989 PCT Int'l Appl. .

OTHER PUBLICATIONS

Sprag et al (1986) PUA883:5494–5497.
Rybak et al (1988) Blood 72:714–20 (Abstract Only).
Umezawa et al., (1989) "Chemical Sensor Mechanisms . . . " Ion–Selective Electrodes, 5, ed. E. Pungor, Pergamon Press.

*Primary Examiner*—Christine Nucker
*Assistant Examiner*—David R. Preston
*Attorney, Agent, or Firm*—Fleit, Jacobson, Cohn, Price, Holman & Stern

[57] ABSTRACT

Biosensors for qualitative and quantitative analysis comprise an amphipathic liquid crystalline membrane composed of a lipid bilayer attached to a recording electrode via bridging anchoring molecules. The lipid bilayer is doped with biologic or synthetic ion channels and is in continuous contact with a bulk aqueous medium on both its surfaces. The bridging anchoring molecules may contain a phospholipid moiety linked to a polyoxylakylene chain terminated with a thiol or thioether residue.

10 Claims, 9 Drawing Sheets

Sequence:

1                                         5                                          10                                      15
NH2—Gly—Ile—Gly—Ala—Val—Leu—LYS—Val—Leu—Thr—Thr—Gly—Leu—Pro—Ala—

Leu—Ile—Ser—Trp—Ile—Lys—Arg—Lys—Arg—Gln—Gln—amide.
20                                        25

Sequence:

NH2–Gly–Trp–Gly–Ala–Val–Leu–Lys–Val–Leu–Thr–Thr–Gly–Leu–Pro–Ala–
Leu–Ile–Ser–Cys–Ile–Lys–Gln–amide.

BIOSENSORS INCLUDING LIPID BILAYER DOPED WITH ION CHANNELS ANCHORED TO A RECORDING ELECTRODE BY BRIDGING MOLECULES

FIELD OF THE INVENTION

The invention relates to biosensors comprising a solvated lipid bilayer attached to an electrode surface via bridging anchoring molecules. The lipid bilayer is doped with biologic or synthetic ion channels. The biosensors are useful for qualitative and quantitative analysis.

BACKGROUND OF THE INVENTION

Biological systems perceive extracellular signals, such as light, smell, nerve-nerve stimuli etc., by the initiation of coupled, cascade-like amplification reactions. In many of these, the initial or intermediate steps in the cascade, involve the opening of membrane-associated ion-channels. In ligand-activated channels, the process is initiated by the binding of the small effector molecule (neurotransmitter, odorant, or flavour) to a specific receptor that is either structurally or functionally coupled to the channel protein. This induces conformational changes in the channel protein that leads to the opening of a pore across the lipid bilayer causing a step increase in the membrane's electrical conductance. Biological channels may be functionally reproduced in artificial lipid bilayers leading to effectorinduced currents essentially similar to those occurring in the biological membranes. By means of the electronic amplification available today, a single channel opening event can be detected.

Small amphiphilic peptides, synthetic or of natural origin, were shown to form ionic channels in artificial bilayers. The conductive path across the bilayer is formed by coordinated aggregation of several peptides to create the walls of an aqueous pore. In addition, by modifying their primary sequences, specific channel properties can be altered. Independently, channel formation can be controlled by restricting the lateral and rotational mobility of the peptides in the plane of the membrane.

An ion channel is therefore a device that controls the flow of ions through the dielectric formed by the core of the lipid bilayer. If a bilayer can be attached to a sensing electrode in such a way that: 1) it is highly stable and 2) it preserves its capacity to serve as a medium in which proteins and peptides may form channels, then a unique type of biosensor may be created.

Interfacing layers of amphipathic molecules with solid surfaces has been known for a long time. The methodology introduced by Langmuir and Blodgett is still used in the development of devices that involve adsorption of phospholipids to electrodes. By this methodology, monolayers of the amphipathic molecules are successively transferred from a water-air interface to a solid surface by its orderly dipping in and pulling out from the water compartment. Due to the amphipathic nature of the molecules and the order of the passes of the solid surface through the water-air interface, the layers alternate their hydrophobic-hydrophilic directionality with respect to the solid surface, thus forming stacked bilayers. When these layers are prepared under humidifying conditions, few water molecules with restricted mobility are trapped within the bilayers. However, these systems cannot support bulk-type solvent water molecules between the bilayers, since a liquid-like interface would actually allow the detachment of outer layers from the inner stacked matrix. Consequently, it is clear that a bulk aqueous medium between the first layer and the electrode surface is absolutely inadmissiable.

The lack of bulk solvent water in all Langmuir-Blodgett devices makes them inadequate for mimicking of biologicallike systems and, in particular, for the incorporation of functional ion-channel-forming polypeptides.

Two examples of devices of the prior art prepared according to the Langmuir-Blodgett methodology are to be found in the Australian Patent Application AU 40123/85 and in the PCT International Application published under No. WO 89/01159.

In AU 40123/85 a solid state electrochemical sensor is disclosed which utilizes a film or membrane adapted to pass ions when selected materials, which are to be detected, are present at the membrane surface. In particular, the electrochemical sensor includes a base substrate, and a layer of material attached to the base substrate for producing electrical current in response to the transport of ions to the layer—this layer actually transforms or converts ionic current to electronic current. Also included is a membrane attached to the layer for transporting ions to the layer from a fluid containing the material or chemical species to be detected, the membrane including gating molecules which interact with the chemical species to thereby allow ions from the fluid to permeate the membrane.

WO 89/01159 describes a membrane comprising a closely packed array of self-assembling amphiphilic molecule, and is characterized in that it incorporates plurality of ion channels, and/or at least a proportion of the self-assembling molecules comprising a receptor molecule conjugated with a supporting entity. The ion channel is selected from the group consisting of peptides capable of forming helices and aggregates thereof, coronands, cryptands, podands and combinations thereof. In the amphiphilic molecules comprising a receptor molecule conjugated with a supporting entity, the receptor molecule has a receptor site and is selected from the group consisting of immunoglobulins, antibodies, antibody fragments, dyes, enzymes and lectins. The supporting entity is selected from the group consisting of a lipid head group, a hydrocarbon chain(s), a crosslinkable molecule and a membrane protein. The supporting entity is attached to the receptor molecules at an end remote from the receptor site. It also discloses a biosensor comprising such a membrane bilayer attached to a solid surface.

SUMMARY OF THE INVENTION

The invention relates to a biosensor comprising an electrode-attached solvated lipid bilayer, doped with either synthetic or biological ion channels. Opening of the channels is induced by interaction with the molecule that is to be detected. This causes a step increase in the bilayer conductance which is sensed by the electrodes.

In particular, the lipid bilayer is an amphipathic liquid crystalline membrane attached to a recording electrode via bridging anchoring molecules and is in continuous contact with a bulk aqueous electrolyte medium on both its surfaces.

The bridging anchoring molecules comprise hydrophilic spacer arms joined to a phospholipid moiety, preferably phosphatidylethanolamine having a polyoxyethylene chain terminated by a residue capable of strong linkage to the electrode material, e.g. an—SH or thioether moiety.

DESCRIPTION OF THE PREFERRED EMBODIMENTS

The biosensor of the invention comprises a reference electrode and a recording electrode to which there is attached, via bridging anchoring molecules, an amphipathic liquid crystalline lipid bilayer membrane which is in continuous contact with a bulk aqueous electrolyte medium, on both of its surfaces, and wherein the bilayer boundary is sealed by an apolar contact between the hydrophobic component of the lipid chain and the apolar wall. The bilayers are doped with synthetic or biological ion channels, whose opening is induced by interaction with a suitable external influence, such as by a ligand to be detected, thus causing a change in the electric properties of the membrane, that is sensed by the electrodes and can be measured.

The preferred lipids according to the invention are phospholipids, e.g. soybean asolectin, and the preferred ion channels consist of proteins or synthetic peptides capable of forming helices and aggregates.

The bilayer which is the core of the device is kept in a liquid crystalline state, since it has to constitute a proper medium in which proteins and peptides can perform their biological specific activities. Thus, channel proteins and peptides have to retain sufficient lateral mobility, so as to permit spontaneous formation of ion channels. Concomitantly, the membrane has to be mechanically stable, so that the bionsensor device, in which it is installed, is rendered a long lifespan. To function properly a phospholipid bilayer must be immersed in a bulk aqueous medium, and thus bulk water must be present at all times on both sides of the membrane.

Anchoring the membrane to the electrode surface is designed to mechanically strengthen the bilayer in a way that evokes the minimal interference possible with the lateral mobility of the other bilayer constituents. To meet this requirement, an approach based on the interaction of cellular membranes to cytoskeleton or to extracellular matrix, has been adopted. The cytoskeleton is a mechanical supportsystem common to all biological cells, which is made primarily of polypeptide ribs that bind to distinct points on the inner surface of the membrane. A similar attachment allows the membrane of cells like erythrocytes or epithelial cells to survive extreme mechanical stresses for extended periods.

Following these natural systems, a novel way for attaching a lipid bilayer to an electrode has been devised which involves the synthesis of an anchor molecule consisting of two major components: a common phospholipid, such as phosphatidylethanolamine (PE), and a highly hydrophilic spacer arm, the end of which is substituted by a residue having high affinity for metals. For example, using phosphatidylethanol-amine derivatives containing oxyethylene chains of different lengths and a thiol or thioether residue at the terminal position as particular anchoring molecules, stable solvated bilayers, which retain the dynamic properties required for channel function, have been attached to gold electrode surfaces, according to the present invention.

Figure 2:
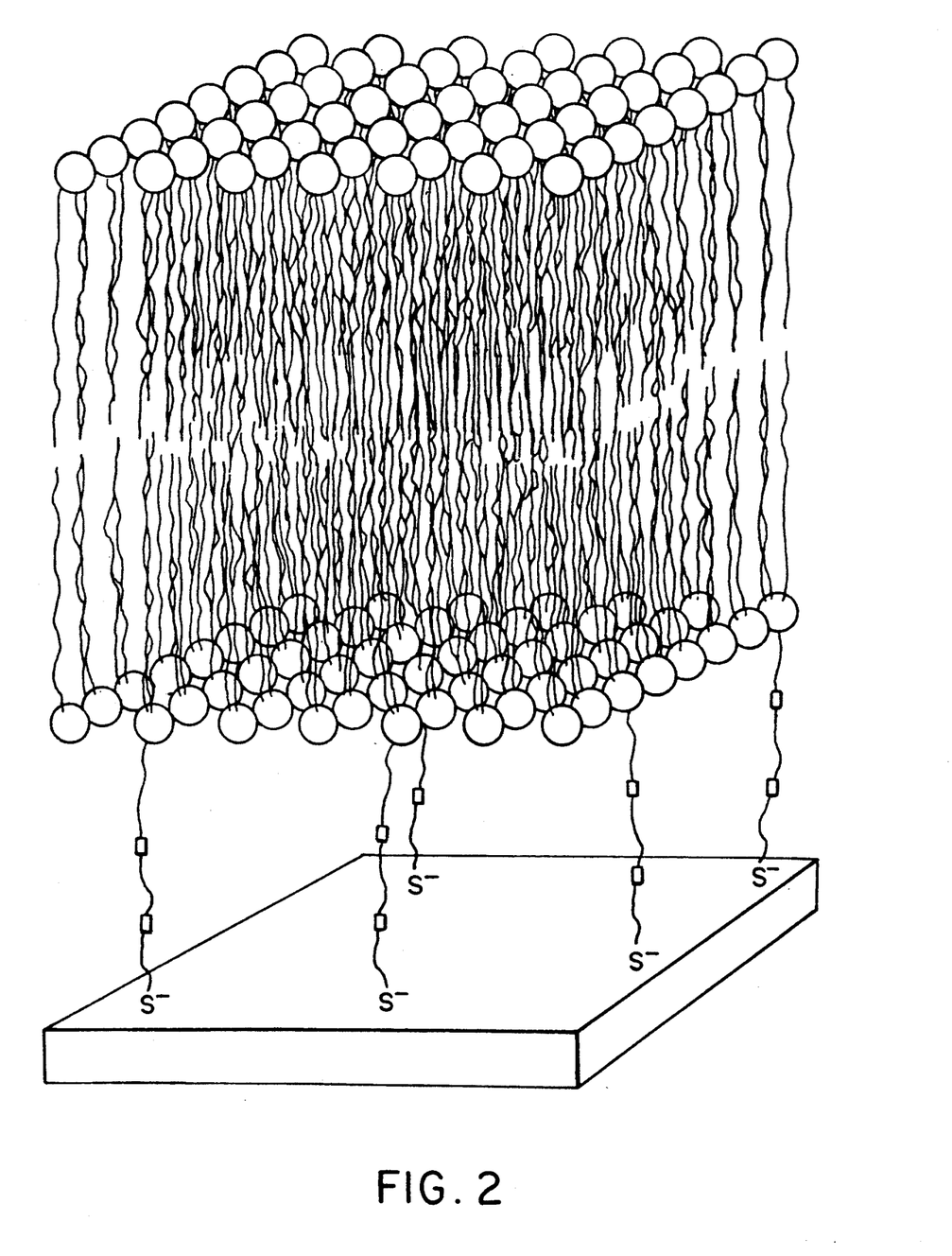
FIG. 2 illustrates a proposed electrode anchored solvated lipid bilayer.

A novel electrode-attached lipid bilayer according to the invention is illustrated in FIG. 2. The novel structure essentially comprises a lipid bilayer attached to the electrode (preferably of a noble metal e.g. silver, gold, platinum, or metal-coated) by means of a plurality of elongated anchoring molecules or polar spacer bridges arranged essentially perpendicularly to both the surfaces of the bilayer and the electrode. The entire structure attached to the electrode, which defines a layer of a certain thickness, is immersed in an aqueous medium, the lipid bilayer structure defining a membrane.

A preferred embodiment of the device consists of an electrode-attached lipid bilayer, doped with either synthetic or biological ion channels. Opening of the channels can be induced by interaction with an effector, which may be the molecule to be detected, magnetic radiation or photon, which causes a step increase in the bilayer conductance, that is sensed by the electrodes. A very high sensitivity can be attained.

Figure 1A:
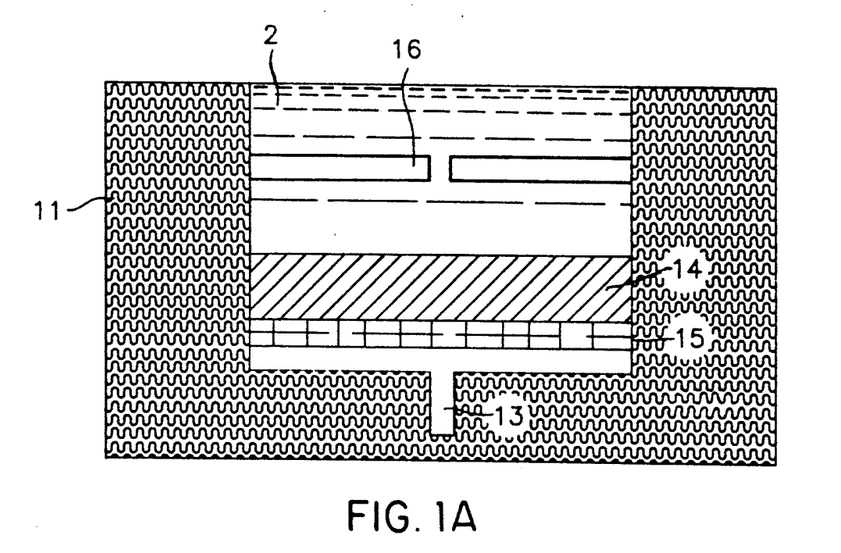
FIG. 1A illustrates the general design of a biosensor of the invention.
Figure 1B:
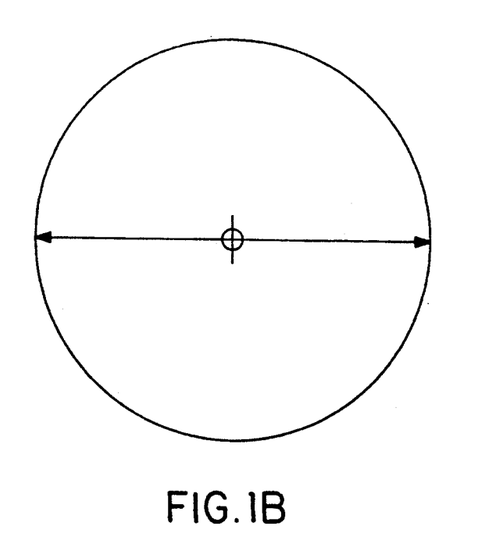
FIG. 1B is a schematic cross-section of the upper surface of a biosensor of FIG. 1A.
Figure 1C:
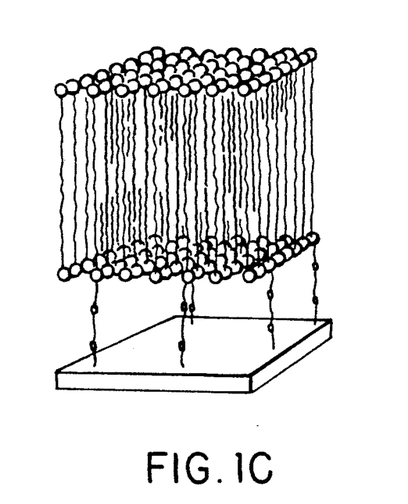
FIG. 1C is a schematic view of an electrode anchored solvated lipid bilayer.

The main features of a biosensor according to the invention are described in FIG. 1. A teflon block (11) contains a circular well (12) at the bottom of which is located a recording electrode (13). To this electrode (13) is attached a phospholipid bilayer (14) (see also insert and FIG. 2) in such a way that there exists a bulk aqueous layer (15) between the bilayer (14) and the electrode (13). The bilayer boundary is sealed at the sides by an apolar contact between the hydrophobic constituent of the phospholipids and the teflon. The bilayer contains, in addition, the ion channel-forming polypeptides (not shown). A second reference electrode (16) is positioned above the bilayer. Instead of teflon, any plastic material that strongly interacts with hydrocarbons may be used, such as polystyrene.

Thus, there is formed an amphiphilic phospholipid bilayer, that maintains firm contact with the bulk aqueous medium at both of its surfaces. This structure yields a liquid crystalline membrane with a thickness in the order of from about 50 Å to about 75 Å, hence capable of supporting embedded functional peptides and proteins. The phospholipid membrane is positioned close to, and parallel to the electrode, yet spaced from it and attached thereto by the bridging anchoring molecules, in the order of about 15 Å to 50 Å length, the entire structure being in an aqueous medium. Biosensors of about 2 mm diameter were tested and found to be highly stable.

The membrane comprises a solvated phospholipid bilayer attached to the electrode through a suitable hydrophilic spacer arm joined to a phospholipid molecule. The arm preferably used is constructed of poly(oxyethylene) chains, wherein n is preferably from about 8 to about 25, but chains containing other polar moieties may be used, such as polyaminoacid chains, all chains terminating with a thiol or a thioether moiety at the far end, or other suitable attachment molecule with a high affinity to the electrode. The hydrophilic portion of these molecules is similar chemically to certain neutral detergent molecules such as the Tritons, in which the hydrophilic portion is made up of a plurality of oxyethylene chains that have a strong interaction with water. This mode of attachment allows the use of mixed lipids in the compositions of the lipid bilayer, where the minor component consists of the phospholipid with the spacer molecule that is used for the attachment, while the bulk of the phospholipids define the bilayer structure.

The present approach for attaching the bilayer attached to an electrode, by means of elongated spacer molecules, has the following novel features:
a. Bulk water is present at the electrode surface and on both sides of the bilayer.
b. Motion of the non-anchored lipids and of the polypeptides incorporated into the bilayer is possible;
c. The bilayer has an adequate degree of stability and a fixed geometry with regard to the electrode surface, that derives from the repetitive attachment of the anchoring molecules to the surface.
d. The absolute smoothness of the electrode surface at an atomic resolution is not critical, in view of said fixed geometry whereby the lipid bilayer will follow the contour of the electrode surface.

The bilayers of the invention are doped with ion channels, whose opening permits the passage of ions through the membrane.

There are at least two ways of inducing channel opening. Depending on the component protein or peptide present in the device, opening of the channel can be induced by two alternative mechanisms. First, a ligand induced opening of pre-existing fixed or assembled channels. The second mechanism is based on the specific removal of a perturbation that prevents amphipathic peptides from spontaneously aggregating to form a channel assembly.

In the first category are the natural channels present in biological membranes, such as the acetylcholine or GABA receptors. These channels can be either highly purified from the suitable cells, or can be genetically engineered. Then, they can be incorporated into the electrode-supported artificial bilayer. The bilayer is then adjusted to support the receptor-channels in their closed state when unoccupied. The binding of a ligand to its specific receptor site induces the conformational change that triggers the opening of the channel, like in the native systems. This approach allows the formation of a device which mimics directly the agonist or ligand perception by the in vivo receptors. In the case of the acetylcholine receptor, the further addition of acetylcholine esterase to the sensor assembly, allows simulation of the susceptibility of the nervous system to both agonists and antagonists. According to this possibility, also hybrid receptor molecules are envisaged by the invention, whose molecules contain a receptive part which interacts with the ligand and a channel-forming part of a second protein. These hybrid molecules may be prepared by conventional genetic engineering procedures.

Figure 5A:
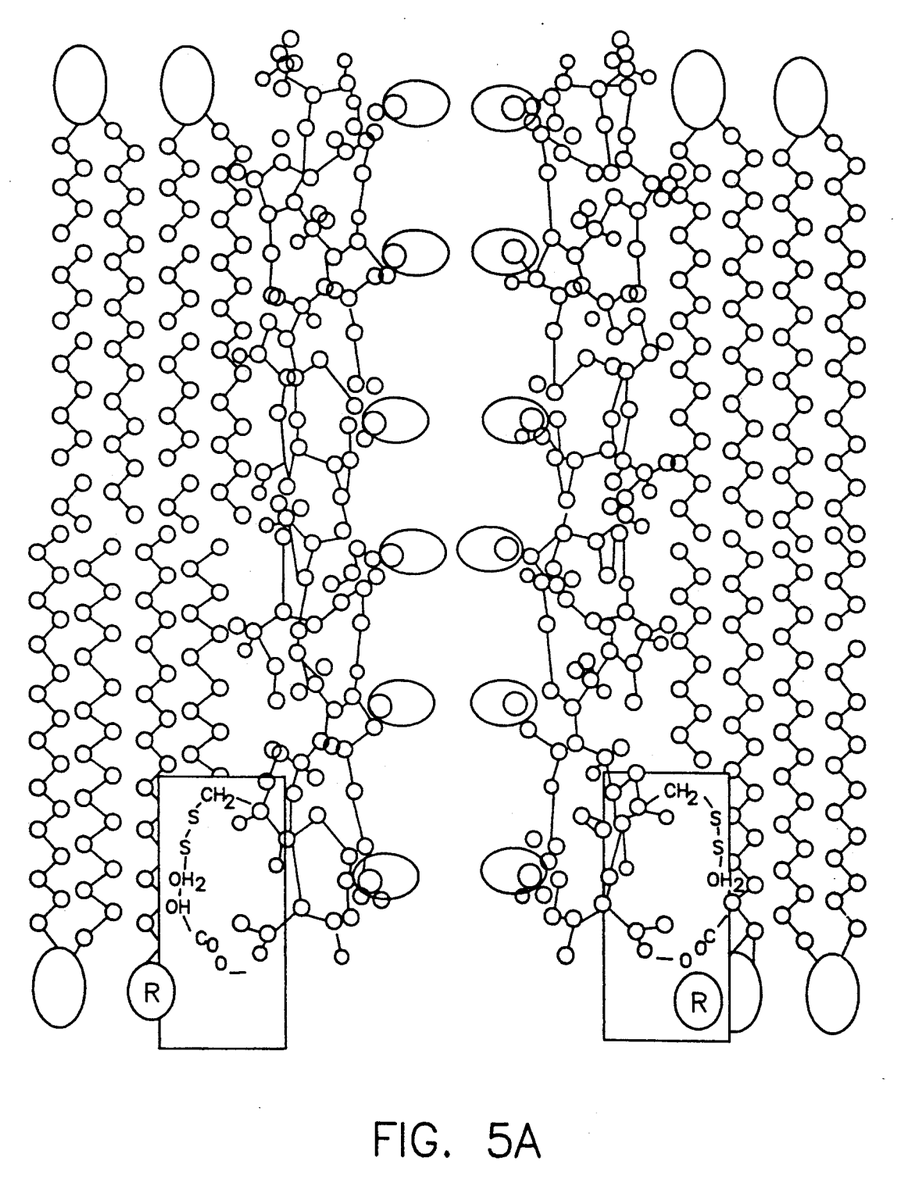
FIG. 5A illustrates a schematic representation of CH-1 as a helical rod aggregate immersed in the lipid bilayer, and shows the polar side-chain groups (open circles not drawn to scale) directed towards the center of the aggregate.
Figure 5B:
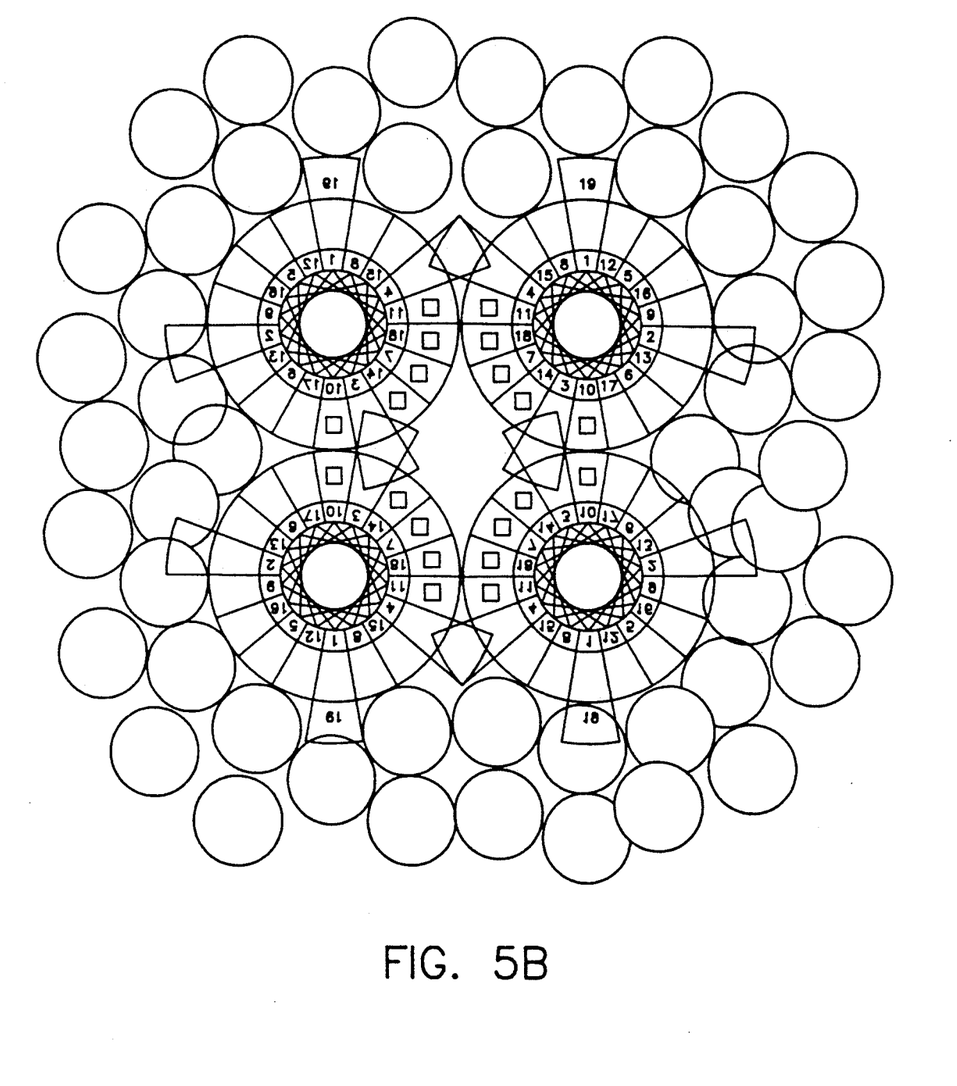
FIG. 5B illustrates a Schiffer-Edmundson helical projection of the aggregate and shows the polar central aqueous pore region. Hapten attachment site is depicted by a rectangle.

A second possibility refers to synthetic peptides, such as melittin or melittin-like peptides, e.g. the novel synthetic peptide herein referred to as CH-1 (described below), that can form assemblies which, upon reaching an adequate degree of aggregation with the proper proximity and axial orientation, function as ion channels (see FIG. 5). In this category, biosensors are constructed based on the use of a hapten as the receptive part of the element and an antibody as an inhibitory ligand component.

Figure 6A:
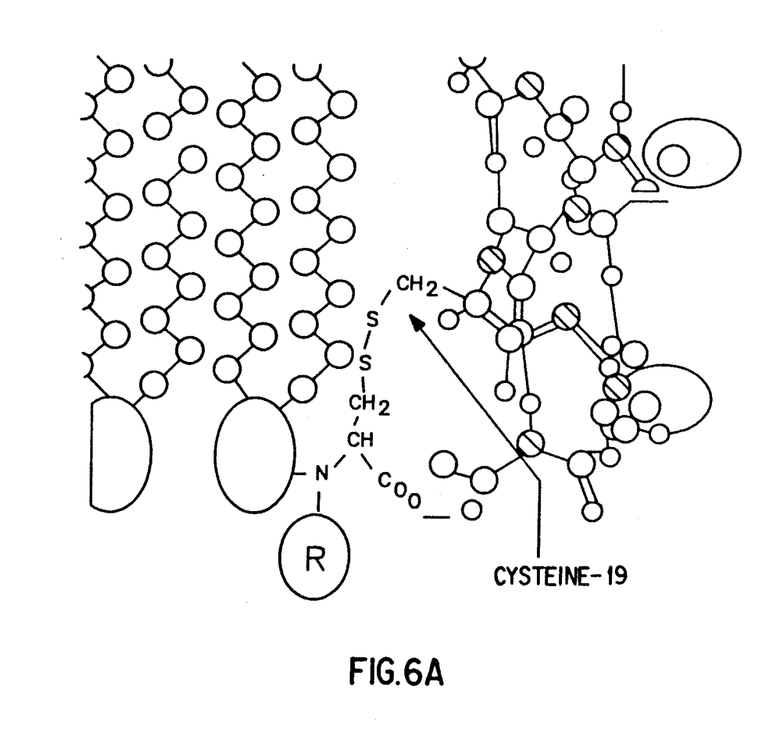
FIG. 6 illustrates the site of hapten attachment to CH-1.
Figure 6B:
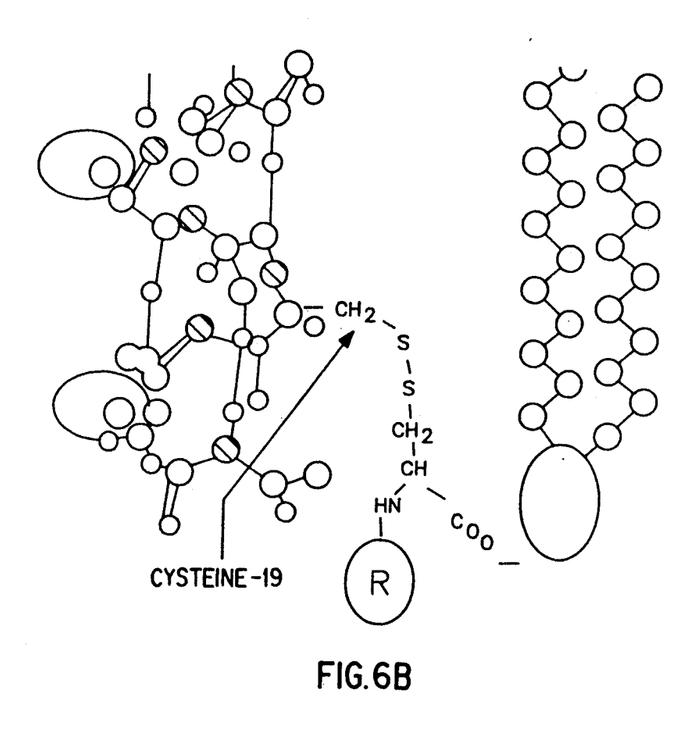
Figure 7:
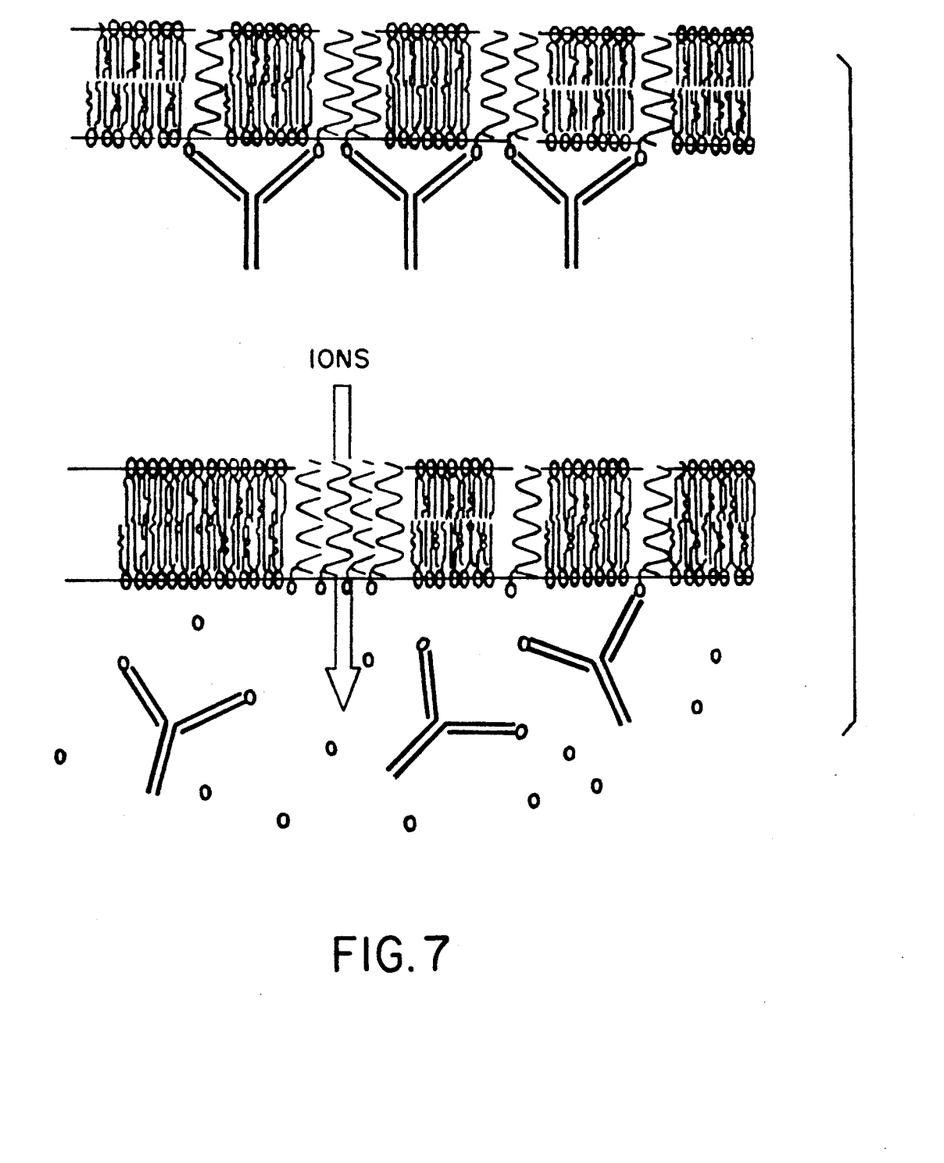
FIG. 7 illustrates schematic representation of the principle underlying channel-forming immunoassay.

Attachment of a hapten moiety to one end of the CH-1 (see FIG. 6), which points at the compartment of the reference electrode when the CH-1-hapten is inserted into the bilayer, allows interaction with monoclonal antibodies directed against the hapten, added to the upper solvent compartment. As long as the antibodies are bound to the hapten-CH-1, they prevent, by steric hindrance, the proper aggregation of the synthetic hapten-CH-1 that is required for the formation of ion channels (see FIG. 7, upper part). Addition of the free hapten or hapten-like molecules to be detected (the analyte), by competing for the antibody binding site and liberating the hapten-CH-1 from interaction with the antibody, allows spontaneous ion channel formation (see FIG. 7, lower part) and its detection because of the large ion conductivity. This method allows the design of biosensors that are capable of detecting molecules for which specific monoclonal antibodies can be produced.

Because of the typically high single channel conductance (between pS and nS), opening of only one channel induced by the binding of a few molecules can be readily detected. The recorded sensitivity of these systems is in the nanomolar range.

As set out above, the interaction of an ion channel or an ion channel site with a chemical entity, results in the opening up of such a channel. In a similar manner, it is possible to interact such a channel with a suitable electromagnetic radiation resulting in the opening up and change of conductivity, such as with electromagnetic radiations of the type of light from the UV to the IR and higher wavelengths. An ion channel can be constructed which comprises a photochromic entity or other photosensitive entity which interacts with light and changes its structure, thus resulting in a change of the conductance of the sensor. Suitable molecules for this purpose are peptides containing stilbene derivatives that can be sensitized to longer wavelengths by suitable sensitizer molecules, such as carbocyanines or merocyanines.

In order to allow the sensor ion channels to return to their closed state, certain relaxation mechanisms are provided. Receptor bound agonists or ligands are removed by an adequate enzyme incorporated into the bilayer or attached to the walls of the cell in the aqueous compartment above the bilayer, which removes the bound chemical entity from the channel-receiving site. The enzyme activity is adjusted so that upon exposure of the device to the substance to be detected, the concentration will transiently rise to open the channels. The miniature dimension of the novel device results in short response time due to diffusion. Thereafter, due to the enzymatic breakdown, the substance to be detected falls to low levels and allows re-initiation of the detection cycle. Since the channels response is very fast, the adequate combination of channels to enzyme can be easily established by experimentation.

Antigen-antibody dependent perturbation of channels is restored by a two step washing procedure. The first removes the detected molecule-antibody complex, and the second serves primarily as a replenishment of free antibody molecules.

Restoration of the electrolyte medium in the aqueous layer between the electrode and the bilayer, is made by reversed ion flux. The electric field is generated between the recording and the reference electrodes. The same mechanism is considered for arresting the ion flux once a sufficient signal is perceived, so that the sensor lifetime is prolonged. The susceptibility of the ion channel opening/closing to externally imposed electrical fields depends on the dipole moment of the peptide, its spatial orientation and mechanical coupling to the helix backbone.

The device of the invention can be an integral part of an electronic system that can readily be adapted to different needs. It is suitable for the detection of a broad spectrum of chemical signals. By control of the lipid components of the lipid bilayer, the system can be made to function at temperatures from 4° C. to 40° C. A suitable coupling of the device with a thermo-regulated Pelttier body can expand the operational temperature to below 0° C. and to above 40° C.

Once a suitable lipid bilayer is attached in a stable functional manner to an electrode, the biosensor can be used to detect any desired molecule for which an antibody can be made or for which there exists a ligand-activated natural channel.

Different components can be used to detect varied signals depending on the requirements.

The invention will now be illustrated by the following non-limiting examples.

EXAMPLE 1

Synthesis of the Peptide CH-1

Figure 3A:
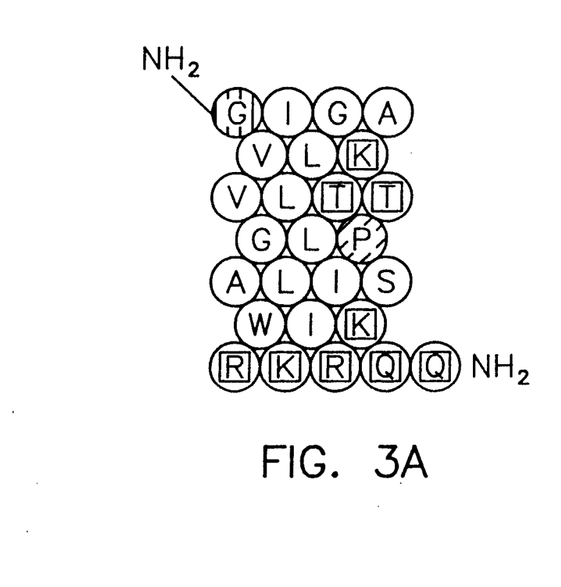
FIG. 3A illustrates a side projection of the structure of bee venom melittin.
Figure 3B:
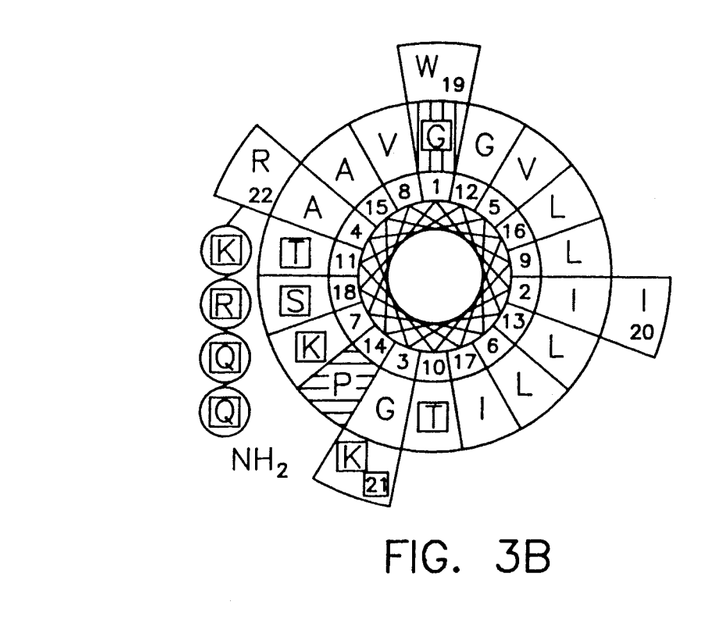
FIG. 3B illustrates a Schiffer-Edmundson projection of the structure of bee venom melittin.
Figure 3C:
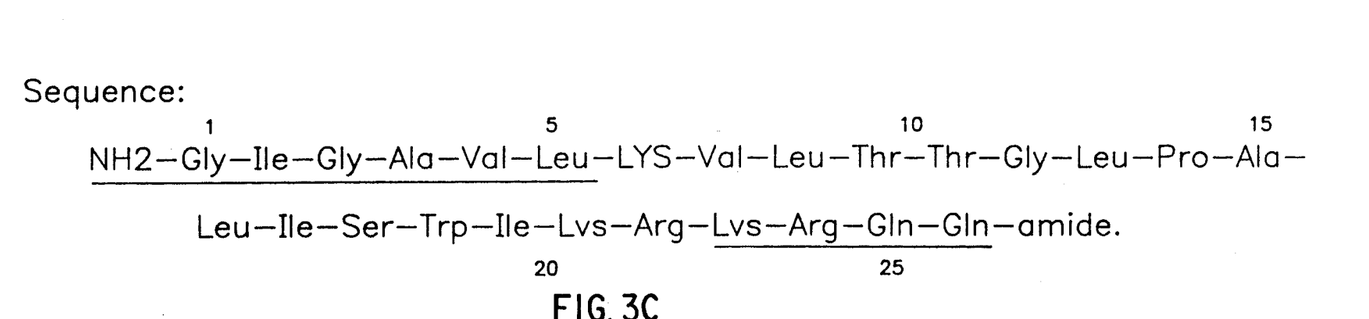

The principles underlying formation of ion channels by small (20-25 amino acid) peptides are not completely understood. It has been suggested that peptides such as alamethicin and melittin (50% of the dry weight of the honey bee venom) form ion channels because they behave as amphipathic-helical-peptides (AHP). That is, the polar amino acids are present in the polypeptide chain with 3, 4 periodicities. On formation of a 3.6 residues per turn α-helix the polar side chains are directed towards the same side of the helical rod. This is exemplified by the sequence of melittin and its side and top projections of the α-helical rod it forms (see FIG. 3).

Melittin has been chosen as the starting point for design of the peptide of this invention. It is water soluble and exists most likely, as a tetramer. Yet, it transfers spontaneously into lipid bilayers probably due to the presence of an apolar 6 amino acid segment (underlined) at the NH$_2$-terminal end of the polypeptide. Once incorporated into the bilayer, it assumes an α-helix secondary structure and forms anion-selective channels. A channel is made of an aggregate of several helices in the plane of the membrane with their hydrophobic side chains in contact with the surrounding lipids. Their hydrophilic side chains are directed away from the lipids and form the aqueous ion conductive pore. However, with time and/or additional incorporation of melittin into the bilayer, relatively large pores are generated and cell lysis becomes dominant. Upon examination of the sequence of melittin (FIG. 3), it was observed that it has a cluster of six basic amino acids (bold and underlined) at the carboxy-terminal end, and it was reasoned that this cluster of basic amino acids could, like poly L-lysine, be responsible for the lytic properties of melittin.

Melittin, like alamethicin, contains a proline in position 14. Interestingly, proline is abundant within the sequence of the ion-conductive segment of most native channels. Proline is an amino acid which presence results in the destruction of the regular α-helix backbone-hydrogen bonds. One or two carbonyl groups of the amide moieties will not be hydrogen bonded and their non-bonding electrons will contribute to the overall polarity and amphipathic configuration of the α-helix.

Based on the above considerations, a homologue of melittin was synthesized that is herein referred to as CH-1 and has the following sequence:

NH$_2$-Gly-Trp-Gly-Ala-Val-Leu-Lys-Val-Leu-Thr-
Thr-Gly-Leu-Pro-Ala-Leu-Ile-Ser-Cys-Ile-Lys-
Gln-amide.

Figure 4A:
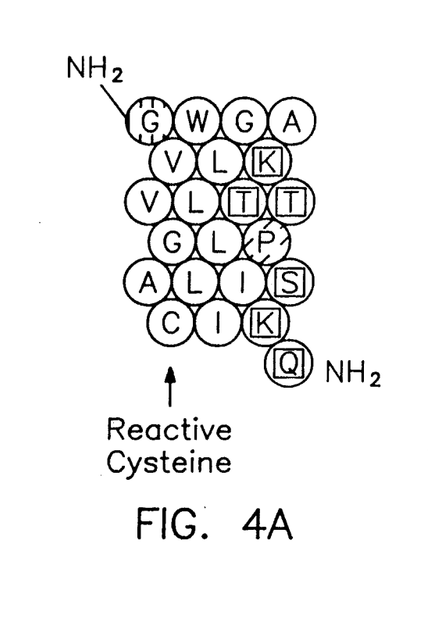
FIG. 4A illustrates a side projection of the structure of peptide CH-1 of the invention.
Figure 4B:
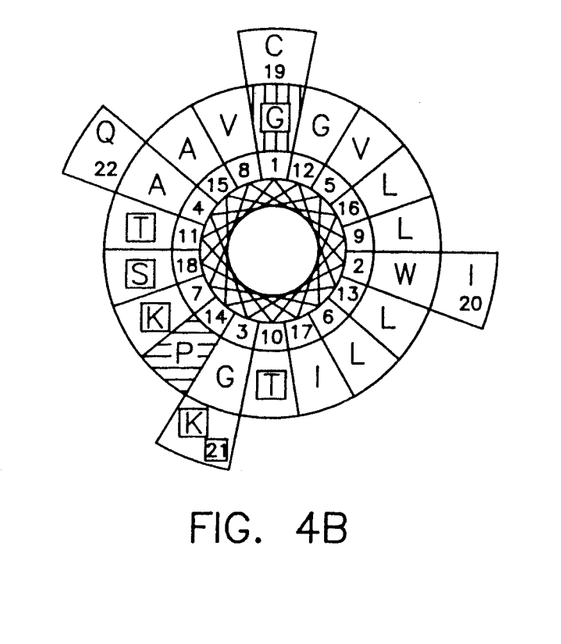
FIG. 4B illustrates a Schiffer-Edmundson projection of the structure of peptide CH-1 of the invention.
Figure 4C:
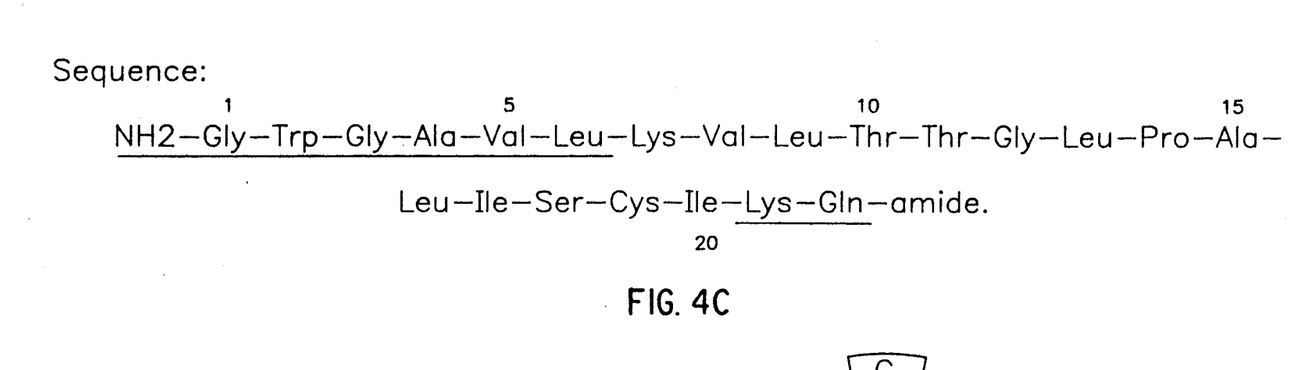

Several significant modifications were introduced into CH-1 (FIG. 4). First, three of the basic amino acids and one glutamine of the carboxy-terminal segment of melittin were removed so as to eliminate lytic properties from CH-1. Second, residues 2 and 19 of melittin were substituted: tryptophan for isoleucine and cysteine for tryptophan, respectively. The rest of the CH-1 molecule is identical with melittin. The cysteine at position 19 was introduced as a reactive center. It permits substitution, by direct attachment or disulfide formation, of fluorescent probes, haptens or peptides containing desirable epitopes, without altering the helical structure. It was protected after synthesis as the methyldisulfide derivative (cysteine-S-S-CH$_3$). On reduction, it forms a reactive group to which may readily be attached fluorophores without altering the peptide CH-1 packing. Most important, cysteine-19 is the reactive center used to form mixed disulfide conjugates with haptens or peptides containing desirable epitopes (see also FIG. 5).

On lateral association, the CH-1 peptide aggregates form ion channels. The cysteine in position 19 allows facile attachment of haptens. For example, a CH-1 derivative with a trinitrobenzene (TNB) containing hapten was prepared. The binding of antibodies e.g., anti-TNB antibodies to the hapten prevents aggregation of the polypeptide. In the presence of free hapten or hapten-like derivatives (the analyte), e.g. TNB or other nitroaromatic derivatives, the CH-1-hapten moieties (e.g. CH-1-TNB) are released by competition from the antibody to form ion channels. This allows construction of a biosensor that can monitor the presence of analytes equal or similar to those of the hapten derivatives attached to CH-1 (e.g. TNB or other nitroaromatic derivatives). Use of cysteine-containing peptide epitopes attached to CH-1 by a disulfide bond are also suitable.

The relative hydrophilic angular sector of the CH-1 α-helix seems to dictate that a stable ionic channel is constructed of a tetramer assembly. FIG. 5 is a schematic representation of CH-1 as a helical rod aggregate immersed in the lipid bilayer. In (A), the polar side chain groups (open circles not drawn to scale) are directed towards the center of the aggregate. Schiffer-Edmundson helical projection of the aggregate (B), shows the polar central aqueous pore region. Hapten attachment site is shown by a rectangle.

It is likely that factors that perturb the aggregation decrease the probability that open channels are formed. The fact that channel opening is due to the transient formation of aggregates due to spontaneous lateral diffusion in the bilayer plane, implies also that any perturbation to the diffusion will decrease the probability of formation of ion channels.

The peptide CH-1 was prepared using a unique peptide synthesizer, based on a conventional solid phase synthesizer with improved coupling and removal methods. The overall yield of 80% was obtained for the 22-step synthesis of CH-1. The peptide was then purified to 99+% yielding single symmetric peaks by HPLC analysis.

Figure 8A:
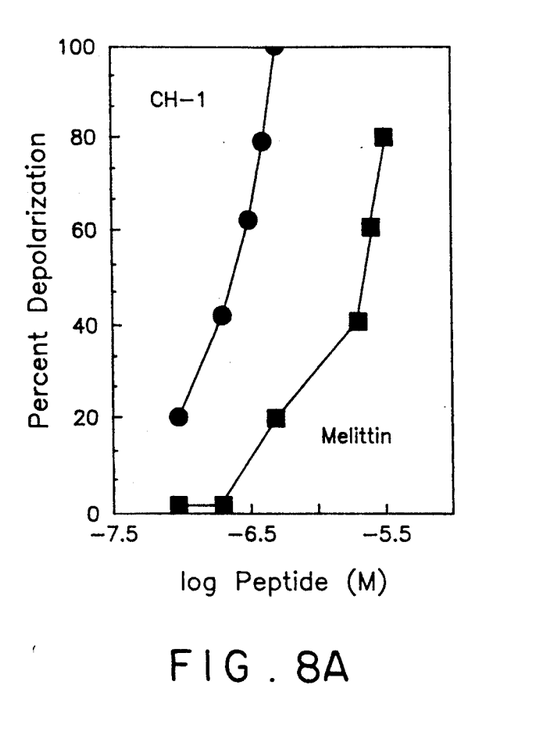
FIG. 8A illustrates the ion channel activity of CH-1 and depicts the depolarization of the valinomycin induced $K^+$ diffusion potential in asolectin liposomes.

The characterization of the channel-forming activity of CH-1 was determined at the macroscopic and microscopic levels. At the macroscopic level, the amount of CH-1 required to collapse a valinomycin potential in liposomes, was determined by the method of Loew et al., that involves the addition of valinomycin to K+-containing liposomes, placed in a sodium medium. This results in a transmembrane potential that induces the movement of a cationic dye into the membrane causing its loss of fluorescence. On addition of CH-1 or melittin, their incorporation into the liposome membrane induces ion-channels which collapse the valinomycin potential and restore the dye fluorescence. It can be observed (FIG. 8A) that CH-1 is more effective in its capacity to collapse the valinomycin potential than melittin.

Figure 8B:
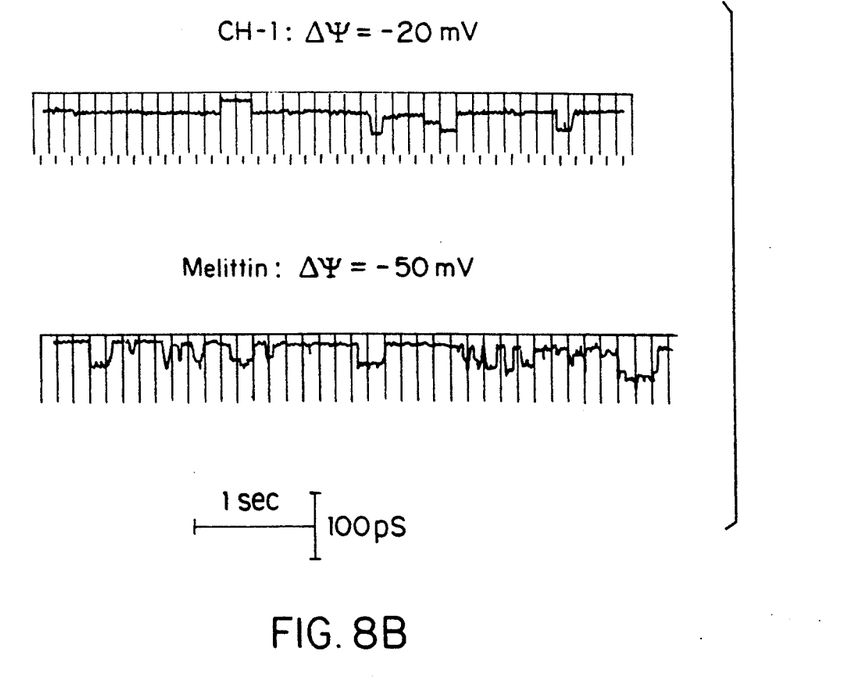
FIG. 8B illustrates single channel activity in a planar lipid bilayer at the tip of a glass capillary.

FIG. 8B shows the microscopic single channel activities of CH-1 and of melittin. These activities were recorded using standard ion-channel measuring equipment using the capillary bilayer method of measurement. It can be seen that equivalent concentrations (0.1 μg of the peptides in 0.1 mM NaCl) of CH-1 and melittin result in defined single channel formation which remain open for a significant period of time.

EXAMPLE 2

Synthesis of the bridging anchoring molecules

A homologous series of phosphatidylethanolamines (PE) derivatized with polyethyleneglycol having a terminal mercaptan radical has been prepared and tested. The synthesis was made along the following general procedure:

The synthesis of phosphatidylethanolamine-N-(oxyethylene)$_{11}$-CH$_2$-CH$_2$-SH was performed as follows: A polyethyleneglycol preparation (average mol.wt 600) was used. It contains on average 12 oxyethylene resides. To react it with phosphatidylethanolamine, it was first converted into the dibromoderivative by reaction with phosphorous trichloride. The aqueous extract was extracted with benzene to remove the low molecular weight fractions and the α,ω-dibromopoly(oxyethylene)$_{12}$ was extracted with chloroform. It was characterized by proton NMR, bromine analysis and thin layer chromatography in 2-butanone/H$_2$O (1:1) where it had an R$_f$ of 0.01. The dibromopolyoxyethylene derivative (in excess) was coupled with phosphatidylethanolamine in tetrahydrofuran-triethylamine by heating in a sealed ampoule. Thiourea was added and the tetrahydrofuran was substituted by isopropanol. Refluxing for 2 h resulted in the conversion of the bromoderivatives to the isothiouronium salts which were then converted to the mercaptans by mild alkaline hydrolysis. The phosphatidylethanolamine-N-poly(oxyethylene)-SH was purified by chromatography in silica gel using chloroformmethanol-acetic acid-water as solvent. The derivative was characterized by the presence of a 1:1 ratio between phosphate and the mercapto group (measured by the liberation of thionitrobenzoic acid from 5,5'-dithio-bis-2-nitrobenzoic acid). In addition it contained two acyl fatty acid chains per phosphate group. This arm supports an aqueous spacing of the order of 30 Å.

EXAMPLE 3

Procedure for the formation of the solvated bilayers at the surface of the gold electrode 3.1. Coating of the teflon walls Prior to the introduction of the gold wire, the well within the teflon block is filled with a drop of hexadecane in hexane, that is allowed to interact with the teflon for 20 min. It is then removed and the well is washed with a solution 0.1 mM NaCl, 0.05M HEPES buffer, pH 7.4.

3.2. Preparation of the electrode surface

The electrode is prepared by insertion of a gold wire from the bottom into the well, such that it seals one end of it. Prior to insertion, the gold wire is cleaned by etching with an acid.

3.3. Preparation of the mixed micelles

Soybean phospholipids were purified by extraction with cold acetone to remove the neutral lipids, dried and then dissolved in chloroform-methanol (2:1). To this solution was added cholesterol in a chloroform solution such that the phospholipid to cholesterol molar ratio was 5:1. In addition, phosphatidylethanolamine-N-ethylene(oxyethylene)$_{10}$ ethylene-mercaptan (the bridging molecule of Example 2) dissolved in tetrahydrofuran was added such that the ratio of phospholipid to the bridging molecule molar ratio was 50:1. In addition, α-tocopherol was added at a molar ratio of 1 α-tocopherol per 200 phospholipids. After mixing, the solvent was removed and the lipids were dispersed to form micelles by the addition of a solution of octylglucoside in 0.1 mM NaCl, 0.05M HEPES buffer, pH 7.4. The octylglucoside was added so that for each phospholipid there are two molecules of detergent. This ratio resulted in the formation of mixed micelles of octylglucoside containing phospholipid, cholesterol and the bridging arm.

3.4. Attachment of the mixed micelles to the gold electrode

The solution of the mixed micelles (detailed in 3.3) is introduced into the teflon well and the micelles are allowed to attach to the gold by means of the bridging arm (from 2 h to overnight at room temperature). After the mixed micelles are attached to the gold electrode, a dialysis film was attached to the teflon well at the end opposite to that of the gold electrode making sure that no air was trapped within the well. The whole assembly was then introduced into a large container filled with 0.1 mM NaCl, 0.05M HEPES buffer, pH 7.4 and the octylglucoside was removed by dialysis. This required 24 h. The dialysis film is removed and the solution above the electrode is carefully removed and replaced several times with 0.1 mM NaCl, 0.05M HEPES buffer, pH 7.4.

3.5. Examination of the solvated bilayer formed

The attachment of the micelles by the arm to the gold is followed by dialysis of the detergent. This results in the formation of a continuous bilayer attached to the electrode and that seals on its sides by interaction with the hexadecane-coated teflon. In addition, the excess lipid forms liposomes that are removed by the washing procedure detailed in 3.4. The placement of an electrode in the upper part of the well allows measurement of the impedance between this reference electrode and the gold electrode. The formation of a bilayer that is attached to the gold electrode and seals on its sides by interaction with the hexadecanecoated teflon is evidenced by the presence of a very high impedance to current flow between the electrodes. The values obtained indicated that the base-line conductance was in the order of 5 to 10 pS. Measurements were performed using the same equipment as that used to measure single channel formation by means of Montal planar lipid bilayers.

EXAMPLE 4

Use of the gold-attached solvated bilayers to measure the concentration of an analyte.

The devices of the invention are useful for a method for the analysis of an analyte in a sample where this sample is contacted with a biosensor comprising a lipid bilayer doped with mellitin-like peptides containing an analyte or analyte-like moiety as the hapten and the whole molecule is bound to an antibody directed against the hapten. In the example detailed here trinitrobenzene (TNB) was used as a hapten attached to peptide CH-1 and the concentration of a free TNB-derivative as the analyte was measured. In the same way, using thyroxine attached to CH-1, free thyroxine can be measured in a sample.

4.1. Attachment of the hapten group to CH-1

N-TNB-beta-alanyl-cysteine was prepared by standard peptide synthesis methods. It was reacted with an equivalent of dithio-bis-nitrobenzoic acid in borate buffer pH 8.0. Upon termination of the reaction (liberation of thionitrobenzoic acid measured at 412 nm), it was added without purification to a solution of CH-1 that had been treated with 0.6 mM DTT at pH 9.0, followed by HPLC to remove the thiomethyl group used to protect the thiol-group of cysteine-19 of CH-1. The reaction was followed by the liberation of the thionitrobenzoic acid. On completion of the reaction, the N-TNB-beta-alanyl-cysteine-CH-1 disulfide formed was purified by HPLC using an acetonitrile gradient.

4.2. Interaction of N-TNB-beta-alanyl-cysteine-CH-1 disulfide with TNP-antibodies and the bilayer attached to the gold electrode The N-TNB-beta-alanyl-cysteine-CH-1 disulfide (hapten-CH-1) is titrated with a monoclonal antibody with a high specificity for TNB-moiety and a high affinity constant. The amount that is required to neutralize the channel activity of the hapten-CH-1 is determined by titrating hapten-CH-1 with the anti-hapten antibody in the presence of a planar lipid bilayer in a Montal set up. Once this stoichiometry is known, the hapten-CH-1 anti-hapten antibody, at the ratio that neutralizes the channel, is added to the bilayer attached to the gold electrode. The basal channel activity measured is negligible. Upon addition of free N-TNB-alanylcysteine as the analyte, the competition of the free TNB-derivative with the hapten-CH-1-anti-hapten antibody complex results in the liberation of the hapten-CH-1, which forms ion channels in the bilayer. The channel activity correlates with the concentration of the hapten-CH-1 liberated, which in turn, correlates with the concentration of the analyte. The concentration of hapten-CH-1 that is determined varies depending on the antibody affinity. In general, because the channel formation can be detected with very high sensitivity, proportionality is observed in the first third of the affinity curve of the anti-hapten antibody for the hapten. With an antibody with an affinity of $3 \times 10^8$ mol $^{-1}$,$1^{-1}$, an average concentration of $10^{-8}$M of the analyte can be detected. Linearity in the response within a given range is adequate with a given antibody. However, each antibody has to be calibrated.

EXAMPLE 5

Procedure for the formation of bilayers containing channel proteins attached to the electrode.

The biosensors of the invention comprising a lipid bilayer doped with a biologic ion channel are useful for detection of a ligand in a sample wherein the sample is contacted with said biosensor comprising ion channels composed of the receptor or of a hybrid molecule comprising the receptive part of the receptor of said ligand.

5.1. Preparation of the mixed micelles containing acetycholine receptor

The acetylcholine receptor was purified by standard methods using affinity chromatography with Naja naja toxin. It was then incorporated into the mixed micelles containing the same components as those described in 3.3. The ratio of phospholipids to acetylcholine receptor was 200 to 1.

5.2. Attachment of the mixed micelles to the gold electrode

The formation of the bilayer attached to the electrode was performed essentially as described in 3.4 above.

5.3. Activity in the presence of acetylcholine

The basal activity observed with the membranes containing the incorporated acetylcholine receptor was somewhat higher than that obtained without any added dopant. The conductivity varied between 10 to 15 pS. Upon addition of acetylcholine to the medium bathing the outer surface of the bilayer attached to the electrode, the appearance of increased noise level and some discrete channel events with different activity levels are observed. This enhanced activity remained for a period of 30 min. The enhanced overall noise level and enhanced conductivity allow detection of the presence of acetylcholine. Without acetylcholine or in the presence of other amines that do not combine with the receptor, the activity remains low. Upon addition of acetylcholine, the signal is definitely increased.

We claim:

1. A biosensor for qualitative and quantitative analysis of an anylate comprising a container defining a containment chamber having at least one wall comprised of apolar material exposed to the containment chamber; bulk aqueous electrolyte medium contained in said containment chamber; a reference electrode located in an upper part of the containment chamber immersed in said electrolyte medium; a recording electrode located at the bottom of said containment chamber; a liquid crystalline membrane comprised of a lipid bilayer doped with ion channels wherein said liquid crystalline membrane is immersed in the electrolyte medium between the reference electrode and the recording electrode; and bridging anchoring molecules attached to the recording electrode on one side and to the lipid bilayer on the other side to anchor the lipid bilayer to the recording electrode in a spaced relationship so that the lipid bilayer is in continuous contact with the bulk aqueous electrolyte medium on both the upper and lower surfaces of the lipid bilayer with the boundaries of the lipid bilayer being sealed by apolar contact with the apolar material of the at least one wall.

2. A biosensor according to claim 1 wherein the lipid bilayer is comprised of a solvated phospholipid bilayer and the bridging anchoring molecules are comprised of a hydrophilic spacer arm joined to a phospholipid moiety.

3. A biosensor according to claim 2 wherein the bridging anchoring molecules comprise a phosphatidylethanolamine residue linked to a polyoxyalkylene chain terminated by a thiol or thioether residue for attachment to the recording electrode.

4. A biosensor according to claim 3 wherein the bridging anchoring molecule has the formula wherein PE—NH is the residue of phosphatidylethanolamine and n is an integer of from about 7 to about 24.

5. A biosensor according to claim 1 wherein the ion channels are proteins selected from a group consisting of natural receptors and hybrid receptors having a receptive part which interacts with a ligand and a channel-forming part of a second protein.

6. A biosensor according to claim 1 wherein the ion channels are synthetic mellitin-like peptides having a hapten as the receptive part and an antibody directed against a hapten as an inhibitory ligand component, the hapten being an analyte or analyte-like moiety.

7. A biosensor according to claim 6 wherein the ion channel is the peptide CH-1 of the formula 8. A method for the analysis of a ligand comprising contacting a sample containing the ligand with a biosensor according to claim 5 wherein the ion channels comprise the receptor to said ligand or comprise at least its receptive part attached to a channel-forming part of a hybrid protein, and the binding of the ligand triggers the opening of the ion channel in the lipid bilayer leading to a change in electric conductivity, and measuring the change in electric conductivity by the recording electrode.

9. A method for the analysis of an analyte comprising contacting a sample containing said analyte with a biosensor according to claim 6 wherein the ion channels are mellitin-like peptides, containing said analyte or analyte-like moiety as the hapten, and which are bound to an antibody directed against the hapten, whereby the antibody molecules are released thus triggering the opening of the ion channels in the lipid bilayer leading to a change in electric conductivity, and measuring the change in electric conductivity by the recording electrode.

10. A method for the analysis of an analyte comprising contacting a sample containing said analyte with a biosensor according to claim 7 wherein the ion channels are mellitin-like peptides, containing said analyte or analyte-like moiety as the hapten, and which are bound to an antibody directed against it the hapten, whereby the antibody molecules are released thus triggering the opening of the ion channels in the lipid bilayer leading to a change in electric conductivity, and measuring the change in electric conductivity by the recording electrode.

* * * * *